United States Patent [19]

Schiller

[11] 4,322,163

[45] Mar. 30, 1982

[54] FINGER IDENTIFICATION

[75] Inventor: Michael Schiller, Riverdale, N.Y.

[73] Assignee: Fingermatrix Inc., North White Plains, N.Y.

[21] Appl. No.: 207,639

[22] Filed: Nov. 17, 1980

Related U.S. Application Data

[63] Continuation-in-part of Ser. No. 42,605, May 25, 1979, abandoned, and a continuation-in-part of Ser. No. 891,497, Mar. 20, 1978, abandoned, which is a continuation-in-part of Ser. No. 844,580, Oct. 25, 1977, abandoned, said Ser. No. 42,605, is a continuation-in-part of Ser. No. 844,719, Oct. 25, 1977, abandoned.

[51] Int. Cl.³ .......................... G06K 9/00; G06K 9/20
[52] U.S. Cl. ...................................................... 356/71
[58] Field of Search ................. 356/71, 371, 394, 446, 356/448; 350/146.3 E; 250/566

[56] References Cited

U.S. PATENT DOCUMENTS

| | | | |
|---|---|---|---|
| 3,443,098 | 5/1969 | Lewis | 350/485 |
| 3,627,991 | 12/1971 | Beall et al. | 356/71 |
| 3,865,488 | 2/1975 | Del Rio | 356/71 |
| 4,120,585 | 10/1978 | DePalma et al. | 356/71 |

*Primary Examiner*—William H. Punter
*Attorney, Agent, or Firm*—McAulay, Fields, Fisher, Goldstein & Nissen

[57] ABSTRACT

A finger pressed against a platen provides a fingerprint object which is scanned by an interrogating beam of collimated light in the form of a slit and that is linearly displaced across the platen. As the slit-beam scans across the back surface of the platen, the reflected light beam is modulated. The modulated beam is imaged onto a linear array of photodiodes to provide a series of output signals indicative of modulation information. The outputs of the diodes are serially interrogated at each of successive scan positions to provide a set of signals containing fingerprint information. The platen has a transparent glass base. A layer of transparent, compressible, resilient epoxy is on the back of the glass base. The epoxy layer has a flat back surface. A thin silver reflecting layer on the back surface of the epoxy provides a flat mirrored surface to reflect the light beam. A further epoxy layer on top of the silver provides mechanical filtering. A lacquer layer at the back protects the platen from wear. When a finger is applied to the back surface, the ridges of the finger distort the underlying layers sufficiently so that the reflected light at the ridge zones is scattered while the reflected light at the valley zones is collimated. This difference in scatter is transformed by an imaging lens to a difference in intensity at the diode array.

12 Claims, 9 Drawing Figures

FINGER IDENTIFICATION

REFERENCE TO RELATED APPLICATIONS

This application is a continuation-in-part of the following applications: (a) now abandoned co-pending application Ser. No. 042,605 entitled "Fingerprint Processing Method and Apparatus", filed May 25, 1979 which patent application is in turn a continuation-in-part of now abandoned application Ser. No. 844,719 having the same title and filed Oct. 25, 1977; and (b) now abandoned co-pending application Ser. No. 891,497 entitled "Finger Identification" filed Mar. 20, 1978, which patent application is in turn a continuation-in-part of now abandoned application Ser. No. 844,580 entitled "Fingerprint Processing Apparatus" filed Oct. 25, 1977.

BACKGROUND OF THE INVENTION

This invention relates generally to a finger identification and finger image processing apparatus. More particularly it relates to apparatus and method for encoding finger image information into machine readable language with apparatus that is simple, inexpensive and reliable.

There are a number of systems that have been proposed for the processing of identification information based on the unique configuration of ridges and valleys in an individual's finger. When such information is taken from an ink impression of an individual's finger it is normally called a fingerprint. The more sophisticated techniques that employ optical techniques tend to provide a more refined, discriminate and accurate identification image; which image applicant has frequently called a fingerpress in order to distinguish it from the more primitive ink fingerprint. However, since both are based on the same unique ridge and valley finger characteristics, it should be understood that the term fingerprint is used by applicant generically while the term fingerpress is used to refer to the actual configuration of the ridges and valleys of the finger when pressed against a surface or to the fairly precise image of such that can be obtained by using certain optical systems. In these optical systems, the finger of the subject individual is placed against the back of a transparent platen and the normally flat finger image on the back surface of the platen is imaged through the front of the platen and projected onto a receiving or processing equipment. This receiving equipment may take the form of a screen, of a camera or of an array of photocells.

For example U.S. Pat. No. 3,138,059 discloses such a system. As described in the '0.59 patent, the finger is pressed against a transparent platen and a light beam is projected against the platen. Light is reflected from the finger to a recorder in the form of a camera. U.S. Pat. No. 4,053,228, issued on Oct. 11, 1977 discloses a holographic identification system the disclosure of which is incorporated herein by reference. As described in the '228 patent, a collimated, coherent light beam is projected against the front surface of a transparent platen. The light is reflected from the back surface of the platen, against which surface the subject's finger is pressed. The reflected light beam is modulated with the finger image and is correlated against a hologram of the same fingerpress to provide identification.

However, systems of this type suffer from a number of disadvantages, formost among which is a high degree of inaccuracy. That is, mismatching can easily occur between the hologram and the image. Mismatching error is reduced by employing accurate alignment procedures but this solution increases the cost and complexity of the system. Aside from the question of alignment apparatus, such systems are extremely expensive as they require beam splitters, devices to change direction of the light beams, focusing lenses, devices to effect the necessary correlations, etc. Additionally, these systems are difficult to maintain and service because of the number of elements comprising the systems and the fact that even the slightest vibration can knock a lens or a mirror out of position.

Accordingly, it is a major purpose of this invention to provide a technique for processing a fingerprint or finger image in a fashion that is simple and unambiguous, that avoids undue messiness, provides a high degree of reliability in operation and that can be implemented in equipment which is relatively trouble free and that requires a minimum of maintenance.

It is a further object of this invention to provide all of the above mentioned objects in a system that provides an accurate and unambiguous finger image or fingerprint image which in turn is susceptible to being encoded into machine readable signals.

In the holographic systems, stringent requirements are placed on the platen. The surfaces of the platen must be completely flat to minimize inaccuracies introduced into the reflected light beam. In general, where a lot of light is lost and where the contrast between the ridges and valleys in the image is low, the platen must be an expensive precision unit.

In addition, build up of finger oil introduces inaccuracies into the system. Often, a latent image is fixed to the platen by the finger oil residue on the platen. The operator must maintain the platen clean by wiping it after each use. However, even if the platen is clean, these systems are sensitive to either too much or too little oil from the finger. Either case may produce erroneous results. Other problems occur when the platen is cold and a warm finger is placed against it. This fogs the platen. While a platen may be preheated to eliminate this problem, such a solution is impractical.

Accordingly, a further object of this invention is to provide a highly accurate and reliable finger identification and processing apparatus that includes a relatively inexpensive platen.

Another object of the invention is to provide a finger receiving platen, for such an apparatus, that is insensitive to the amount of oil on a finger.

A further object of the invention is to provide optical fingerprint processing apparatus with greatly enhanced optical contrast between the valley zones and the ridge zones of the finger image.

BRIEF DESCRIPTION

In brief, a laser provides an interrogating light beam which is shaped by two cylindrical lenses into a slit-beam of light. This beam is collimated and scanned across a finger placed against a platen. The finger is pressed against the back surface of the platen and provides a fingerprint object that is constituted by a series of ridges and valleys. The beam is directed towards the front surface of the platen, at a slight angle to normal, and passes through the transparent substrate of the platen to be reflected from the fingerprint object as a modulated beam. The platen may have a deformable resilient layer that conforms to the pattern of ridges and valleys and that enhances the modulation of the light beam. The light beam is scanned across the finger by a linear displacement scanning technique that maintains the angular relationship between the interrogating light beam and the plane of the platen throughout the scan. At any position of the scan, the light beam is modulated by the object being scanned to produce light and dark spots corresponding to finger valley and ridge zones. This reflected modulated signal is projected on a linear array of photodiodes; 1,064 photodiodes in one embodiment. An imaging lens between the platen and the photodiode array projects an image of the fingerprint at a plane in space that, depending on the choice of platen, is either at or displaced from the plane of the photodiode array. Each photodiode responds to either relatively light or dark spots by producing a corresponding signal. These signals are serially interrogated to provide a digital output that is a series of electrical signals representing fingerprint information. An encoder is coupled to this scanning circuit and to the circuit that interrogates the photodiodes to make sure that the modulated slit-beam of light is interrogated at about 1,000 regular predetermined intervals during its scan across the finger involved. By providing a mechanical optical scan in one direction and an electronic scan of the diodes in the orthogonal direction, a simple implementation is provided to provide a two dimensional scan with only a one dimensional displacement motion.

A preferred platen is composed of six layers. The thickest layer is a glass substrate one surface of which forms the front surface of the platen. On top of the glass substrate is a highly deformable, highly resilient epoxy layer that provides a very flat back surface. On top of the epoxy layer, a very thin (3,000 A thick) reflective silver layer is deposited. The silver layer is flat because it is deposited on the flat surface of the epoxy. The silver layer provides a mirrored surface to reflect the incident collimated light beam. The fourth layer is a fairly thin (for example, 0.05 mm. thick) layer of the same epoxy material. The fifth layer is another very thin reflective silver layer. And finally a thin (approximately 0.025 mm. thick) lacquer layer is deposited on top of the silver layer to protect the silver from mechanical wear. The subject's finger is applied to the lacquer. When so applied, the epoxy deforms sufficiently to conform to at least the ridges. The result is a topographical map of the ridge and valley structure at the reflective surface that differentially scatters the incident light. The ridges scatter the incident light substantially more than do the valleys. This provides a modulated reflected light beam. The use of the reflective layer provides a greater light intensity than when the reflective layer is omitted. In this multi-layer sandwich, the touching surface is isolated from the optically active surface and shields the optically active surface from the effects of temperature changes. The lacquer defining the back surface of the platen provides a durable protection to the delicate extremely thin silver reflective layer. These various layers also smooth or filter the ridge breaks in the input finger to provide a more usable and useful topographic map of the finger in the optically active silver layer surface.

BRIEF DESCRIPTION OF THE DRAWINGS

FIG. 3 is a schematic optical diagram of a second embodiment of the apparatus constructed according to the present invention.

FIG. 4 is a sectional view orthogonal to the plane of FIG. 3, to an enlarged scale, of the movable platen portion of the FIG. 3 apparatus.

FIGS. 5 and 5A are a detailed sectional view, in somewhat schematic format, of one platen that may be used in the FIG. 1 and FIG. 3 apparatus with a finger impressed thereon. FIG. 5A is a very much enlarged view of the indicated portion of FIG. 5. It whould be understood that FIG. 5A is even more schematic than in FIG. 5 and only schematically represents what is believed to be the relation between platen and finger ridges and valleys.

FIG. 6 is a view comparable to that of FIG. 5A, illustrating a second embodiment of the platen that may be used in the FIG. 1 and FIG. 3 apparatus. The FIG. 6 platen incorporates a reflective layer 96.

FIG. 7 is a schematic cross sectional view of a third platen illustrating a presently preferred embodiment having five layers on top of a glass substrate.

DESCRIPTION OF THE PREFERRED EMBODIMENTS

The various embodiments described below differ from one another in two major respects. One distinction has to do with what it is that is moved to effect the light beam scan. The other distinction has to do with the type of platen employed to provide the fingerprint or finger image that is interrogated.

Figures 1, 8:
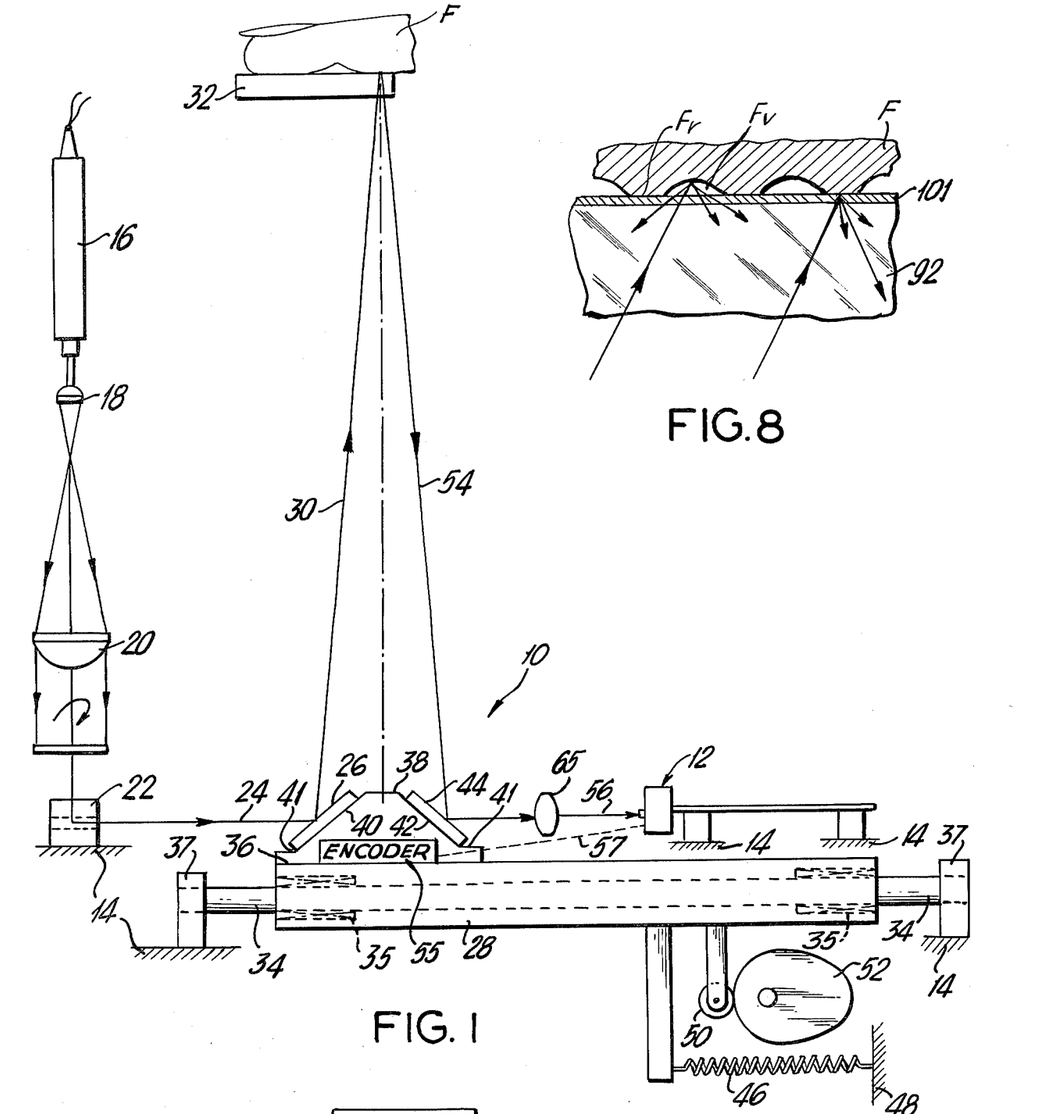
FIG. 1 is an optical and mechanical schematic drawing of a first embodiment of a fingerprint processing apparatus constructed according to the present invention.
FIG. 8 is a view comparable to that of FIGS. 5A. and 6 illustrating a fourth platen having an anti-reflective coating.

In the FIG. 1 embodiment the interrogating light beam 30 is moved so that it scans across a stationary finger F. By contrast, in the FIG. 3 embodiment a platen 64 and finger F on the platen moves across a stationary interrogating light beam 61, thereby effecting the scan.

Figures 3, 4, 5, 5A, 6, 7:
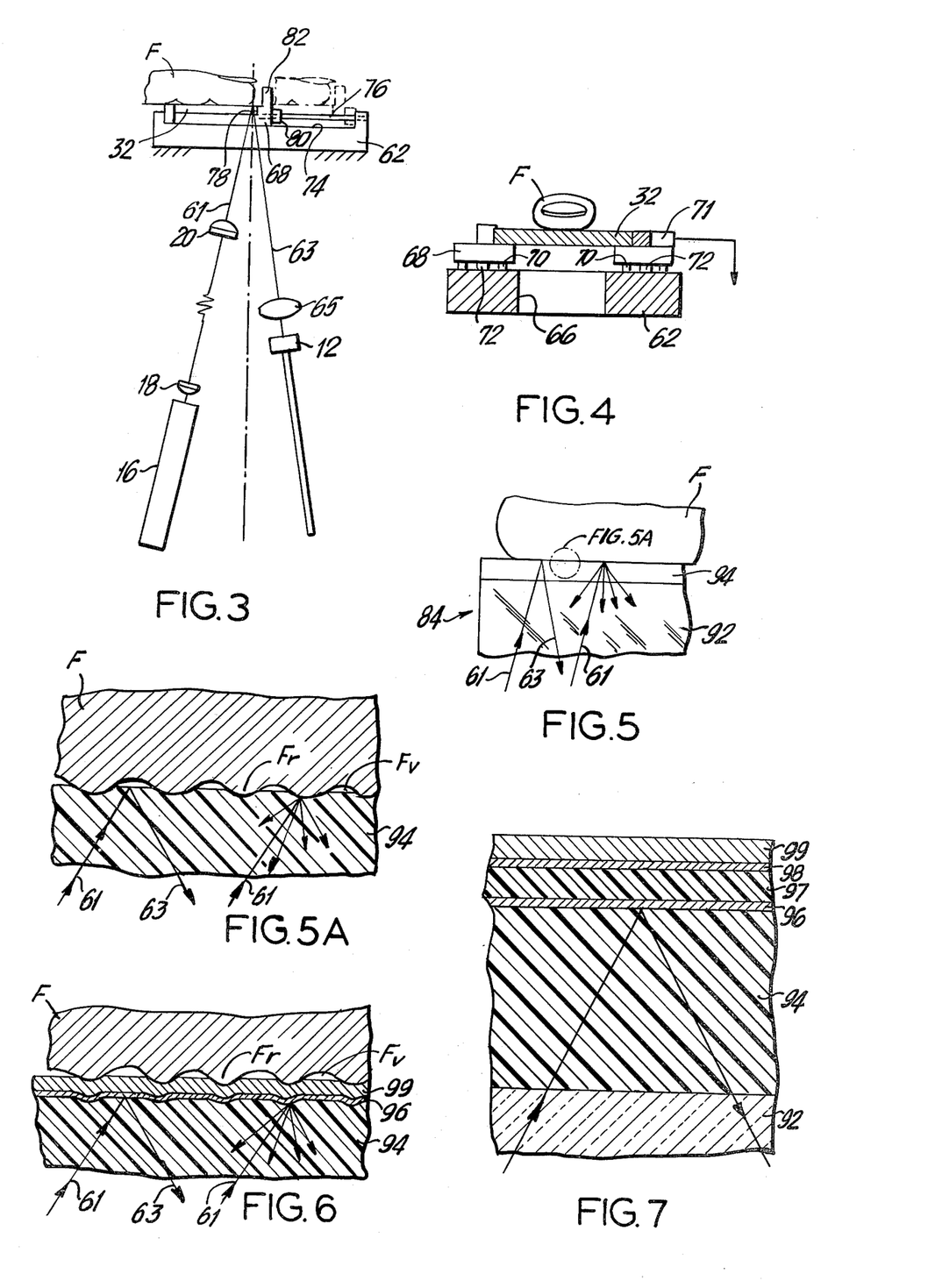

The platen illustrated in FIG. 5 includes a deformable, resilient layer 94. The platen of FIG. 6 includes a reflective layer 96 under the deformable, resilient layer. The platen of FIG. 7 includes a second deformable layer 97 as well as a second reflective layer 98. The platen of FIG. 8 is a rigid glass platen with an anti-reflective layer 101.

The term collimate is used herein to refer to a light beam in which the light rays do not scatter. It is not essential that the light rays all be parallel to one another (except at its focal point). It is only essential that they do not cross over one another. Thus, a collimated light beam as used herein might be diverging, or parallel, or converging. In one embodiment of this invention the collimated light beam converges at an angle of a few degrees. Accordingly it should be understood that in the specification and claims, "collimate", or "collimation" is used as defined above. The laser 16 described provides a beam of coherent light. Coherent light is required in a holographic system. However, in the non-holographic embodiments described herein, the light beam does not have to be coherent. What is important is that the light beam be collimated in the broad sense of collimation as defined above.

THE FIG. 1 EMBODIMENT

One embodiment of the apparatus constructed according to the present invention is designated generally by the reference numeral 10 in FIG. 1 and includes a linear photodiode array 12 mounted on a support 14. The photodiode array 12 is conventional in construction and may, for example, comprise photodiode array Model No. CCD 131 manufactured by the Fairchild Semiconductor Division of Fairchild Camera & Instrument Co., of Mountainview, Calif. This particular array comprises 1,064 photodiodes that extend in the longitudinal direction (i.e., along a line going into the paper in the configuration of FIG. 1). The diodes are aligned in contact with one another and each diode is about 0.02 mm. on a side. Accordingly, the shape of the light receiving opening of the array is in the form of a slit wherein the long dimension of the slit corresponds to the longitudinal direction of the array.

The source of the light beam is a laser 16. The laser 16 normally produces a circular light beam of relatively small diameter in the order of approximately one millimeter. Cylindrical lenses 18 and 20 are positioned in the path of the light beam downstream from the laser 16 to convert the shape of the light beam into a slit. As is conventional, the cylindrical lenses 18, 20 change the beam dimension along one axis and also collimate the beam along this axis. In an actual embodiment, the beam was stretched and collimated to about 20 mm. along one axis. The transverse axis of the beam remains one millimeter so that the shape of the interrogating beam 30 has a slit format roughly conforming to the format of the linear photodiode array 12.

To aid in vizualization, the laser 16, the cylindrical lenses 18, 20 and the mirror 22 in FIG. 1 are rotated 90° to show the elongated light beam in the plane of the FIG. 1. In practice, these elements have an orientation that is rotated 90° from that shown to be consistent with the orientation of the rest of the apparatus as shown in FIG. 1. In FIG. 1, the interrogating light beam 30, the reflected modulated light beam 54 and the diode array 12 all have their long dimension perpendicular to the plane of the FIG. 1.

Although a laser beam is shown, the light source need not be a laser not even a source of coherent light. It is important however that the interrogating light beam 30 be collimated to maximize the differential scatter in the reflected light beam 54. One benefit obtainable with a laser is that there is little or no divergence of the beam of light. Thus, since the laser produces a light beam having a dimension of approximately one millimeter along the small dimension, no lenses will be required to change this portion of the beam and still maintain the slit dimension approximately one millimeter. This reduces the overall cost of the system and also eliminated the need for any complex focusing arrangement.

In order to get a useful output out of the diode array 12, it is important that the level of light intensity incident on the diode array be significantly above a threshold where a bright spot of light is involved and significantly below that threshold where a dark spot is involved; these spots of dark and light representing points on the ridges and valleys of the finger. By forming the light beam into a slit and then using that slit light beam to scan across the finger pressed against the platen, the level of light intensity available is much greater than in the arrangement shown, for example, in the U.S. Pat. No. 4,053,228 wherein the laser light beam is explained so that it covers the entire area of interest of the finger involved. In contrast with this arrangement in U.S. Pat. No. 4,053,228 the shaping of the light beam into the slit and the scanning of the finger with that slit light beam provides sufficient intensity of light at the diode array 12 to provide a signal level at the diode array 12 which permits a rapid interrogation of the diodes at each scanning point.

The mirror 22 reflects the shaped light beam as beam 24 toward mirror 26. The mirror 26, affixed to a movable support 28, reflects the light beam 24 as beam 30 to platen 32. The platen 32 is adapted to receive a finger F thereon with the fingerprint (more accurately, a flattened pressed finger surface) in contact with the upper surface of the platen. The platen 32 may be a transparent optical device the operation of which is described more fully in my U.S. Pat. No. 4,053,228.

The support 28 is movably mounted for reciprocating movement on arms 34 positioned at each end of the support and slidingly received in bores 35. The arms are supported by posts 37 upstanding from the support 14. Mounted on the top surface 36 of the support is a member 38 having side walls 40 and 42 which terminate in shelves 41. In a preferred embodiment, the sidewalls 40 and 42 form an angle of 42.5° with respect to the horizontal, for reasons noted in greater detail hereinbelow. The mirror 26 is affixed to the wall 40 and a mirror 44 is affixed to the wall 42.

A spring 46 between the support 28 and a wall 48 biases the support 28 toward the right, as taken in FIG. 1. An idler roller 50 is rotatably mounted adjacent the right-hand end of the support 28, as shown in FIG. 1. A motor driven cam 52 is drivingly connected with the idler wheel 50. The cam is shaped so that upon rotation of the cam by the motor the support 28 is driven to the lift. As the cam rotates to the position shown in FIG. 1, the spring 46 returns the support 28 to its right-hand position.

The mirror 44 is in the path of a reflected modulated beam 54 from the platen 32 and reflects the light beam 54 to the diode array 12. The beam 54,56 is modulated with fingerprint information from the platen 32 as noted in detail below.

The angle of the mirror 26 causes the interrogating light beam 30 to strike the platen 32 at an angle 5° off normal. That is, the angle of incidence of the beam 30 with respect to a line perpendicular to the platen 32 is 5°. Similarly, the angle that the reflected beam 54 makes with the normal is also 5°. This insures that the reflected beam 54 will diverge from the interrogating beam 30.

The fingerprint information is modulated onto the slit light beam 30 when the finger F is pressed against the platen 32. The mode of modulation contemplated involves differential scattering of the light incident at valley zones and ridge zones. Where the platen used has an anti-reflective coating of the back surface thereof this mode of modulation may also incorporate differential absorption and reflection from the ridge and valley zones as explained in U.S. Pat. No. 4,053,228. Other modulation implementations are explained in connection with the discussion of the platen structures shown in FIGS. 5, 6 and 7.

More specifically, when a finger F is pressed against the back surface of the platen 32, a surface object is created. That portion of the incident light which is reflected from the finger object is modulated by the ridges and valleys of the finger to provide a reflected light beam 54 that carries the fingerprint information. A lens 65 serves to project an image of the finger object to an image plane downstream. Depending on the platen used, the diode array 12 may be at the image plane or displaced from the image plane. As a result, the modulated slit light beam 56 striking the diode array 12 will contain light and dark spots which are indicative of the fingerprint information. This information is unique for each fingerprint and therefore provides encoded fingerprint information which can be retrieved or otherwise processed as desired by the operator.

The incident light beam 30 is scanned across the finger (from right to left as taken in FIG. 1). The light beam information is synchronized with the output from the diode array 12 by an encoder 55 which produces synchronizing signals that are applied to scanning circuitry by lead 57. The encoder 54 is conventional and produces a signal each time the support 28 moves an incremental distance. In the array 12 each of the diodes are about 0.02 mm. (about one mil.) on a side. The encoder 54 produces a synchronizing signal each time the support moves 0.02 mm. While any type of encoder may be utilized, in practice an optical linear encoder has been used to generate synchronizing signals.

Figure 2:
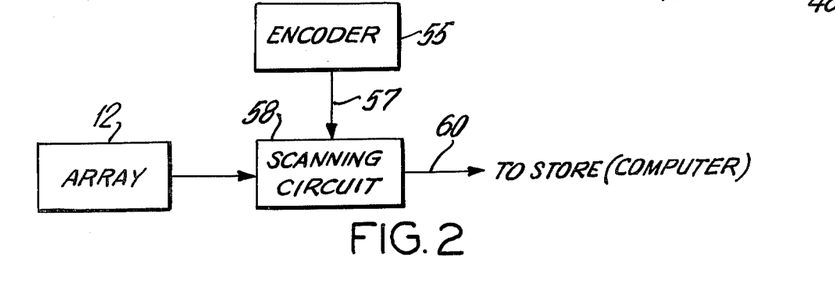
FIG. 2 is a block diagram illustrating the arrangement for encoding the fingerprint information.

In operation, the finger to be examined is placed on the back surface of the platen 32. The laser 16 is energized to produce a slit light beam 30 that impinges on the finger pressed against the back surface of the platen 32. This light is modulated and reflected as light beam 54, 56 to the diode array 12. Simultaneously with the energization of the laser, the encoder 28 produces a synchronizing signal which is applied to a scanning circuit 58 (FIG. 2) via the lead 57. The scanning circuit 58 is conventional in construction and is adapted to sequentially interrogate each one of the photodiodes comprising the array 12 in response to the synchronizing signal. Thus, the output of the scanning circuit 58, which may comprise a train of pulses for each scan line, is connected to the store or computer via a lead 60 so that the fingerprint information can be processed.

The cam 52 is energized simultaneously with the laser 16 so that as the cam 52 rotates, the support 28 moves toward the left as taken in FIG. 1.

As the support 28 moves 0.02 mm. towards the left, the slit light beam similarly moves 0.02 mm. and the modulation of the reflected light beam 54 changes in accordance with the ridges and valleys of the finger. The encoder 54 again produces a synchronizing signal which causes the scanning circuit to again interrogate each one of the photodiodes comprising the array 12 to produce a second train of pulses representative of the fingerprint information in the second scan line.

This operation continues until the entire fingerprint or finger object has been scanned by the slit light beam 30. It is to be understood that the interrogation of the diode array is accomplished electronically at a rate much faster than the rate of movement of the support 28 so that all diodes will have been interrogated before the slit light beam is indexed to the next scan line.

One advantage of the scanning structure shown in that it is a linear displacement scanner. Thus displacement along a straight line of the mechanism, including the mirrors 26 and 44, causes the interrogating slit light beam 30 to be displaced without changing the angular relationship between the interrogating beam 30 and the finger object being scanned and thus without changing the angular relationship between the reflected modulated light beam 54 and the finger object being scanned.

THE FIG. 3 EMBODIMENT

FIGS. 3 and 4 illustrate an arrangement in which the finger F is moved relative to the interrogating light beam 61 to effect the mechanical scanning operation. This is by contrast with the FIG. 1 embodiment where the interrogating light beam 30 is moved relative to the finger F. However both embodiments employ the basic concept of (a) a linear displacement scan between a slit light beam and a platen and (b) a synchronized orthogonal electronic scan of a linear photodiode array 12.

The arrangement shown in FIG. 3 includes a fixed support 62 on which the optical platen 32 is movably mounted. The support 62 has a central channel opening 66 through which the interrogating light beam 61 passes to impinge on the platen 32 and the reflected modulated light beam 63 passes to be further processed. The platen 32 is on a carriage 68 that rides on the upper surface of the support 62 by means of roller bearings 70. Affixed to the carriage 68 is an encoder 71 similar in construction to the encoder 54. Additionally, the carriage 68 is maintained in place by tracks 72 on the support 62 which are received in appropriate recesses in the underside of the carriage.

As shown in FIG. 3, the upper surface of the support 62 has a recess 74, the length of which is substantially longer than the carriage 68. A rod 76 extends between one end of the recess 74 and the carriage 68 and is adapted to be slidingly received in an opening 78 within the carriage. A speed reducing device 80 is connected to the carriage 68 and receives the rod 76 therethrough and is adapted to increase the coefficient of friction between the rod and the carriage to limit the speed of forward movement of the carriage 68 within the recess 74. For example, the device 80 may comprise a plurality of felt washers that receive the rod therethrough in a tight frictional fit.

In operation, the finger F is placed on the platen 32 with the tip of the finger in abutment with the end stop 82 of the carriage. The slit beam 61 from the laser is positioned so that it will impinge at the forward end of the finger when the elements are in the position shown in FIG. 3. The encoder 71 produces a synchronizing signal that causes the array 12 to be interrogated. Thereafter, the finger F exerts a continuous pressure in the forward direction thereby causing the carriage 68 to move toward the right, as taken in FIG. 3. As the carriage moves, its speed is limited by the device 80. Thus, as the finger moves relative to the light beam, the entire fingerprint or finger image is scanned in the manner noted above. The speed limiting device 80 prevents generation of a synchronizing signal while the array is still being interrogated from the preceding scan.

THE PLATEN—IN GENERAL

The linear displacement scanning technique of this invention has been described in connection with two embodiments without specifying the detailed nature of the platen 32 employed. A number of different platen devices have been developed to provide an improved and more useable image than hitherto has been available. Four different platen arrangements are described in connection with FIGS. 5, 6, 7 and 8 respectively. An essential part of the functioning of all four of these platens is that they provide a means whereby the degree to which the reflected light is scattered from under the ridge zones significantly differs from the degree to which light is scattered from under the valley zones.

This differential scattering results in differential processing of the reflected beam by the imaging lens 65 to provide differential intensity, at the array 12, representing ridge and valley zones.

Imaging lens 65 is a simple lens and its ability to focus a reflected light ray as part of the image of the object on the platen created downstream of the lens 65 depends upon the angle at which the reflected light ray is incident on the imaging lens 65. Reflected light which remains collimated is received by the lens at an angle essentially normal to the plane of the lens. Such light, and any reflected light within a few degrees off normal to the plane of the lens will be focused not only at the image plane but also at substantial distances upstream and downstream from the image plane.

As the angle of the reflected light that is incident on the lens 65 deviates further from normal to the plane of the lens, the lens 65 will for a number of additional degrees be able to refocus that light as part of the image of the image plane. However such light will be rapidly defocused above and below the image plane.

Reflected light which is substantially scattered so that it is incident to the lens 65 at angles that deviate substantially from normal will not be refocused at the image plane or at any other plane upstream or downstream from the imaging lens.

The term "angular pass band" will be used herein in connection with the lens 65 to refer to that angular range within which the lens 65 will substantially refocus incident light at the image plane. Light that is scattered outside the angular pass band will simply be lost to the system in that the lens 65 will not be able to use such light to provide an image of that portion of the finger object which has so scattered the light. It should be understood that within the angular pass band significant collimation is lost for light rays which are scattered at the greater angles within the angular pass band and that collimation or substantial collimation is maintained only for light rays which are reflected at angles well within the center of the angular pass band.

Thus, depending on the relative differential scattering of the reflected light from under the ridge zones and the valley zones, the lens 65 will provide more or less focusing or defocusing of the two zones either at the image plane or removed from the image plane as is explained in greater detail in connection with the following description of each of the four different platens that have been developed and tested. What may be useful is to keep in mind that the basic notion behind all of the viable platen arrangements is the generation of differential scattering in the reflected light beam which is converted to differential intensity for detection and reading at the array 12 by the use of an imaging lens 65.

THE FIG. 5 PLATEN

The FIG. 5 platen 84 has two layers. The two layers are a five millimeter (mm) thick transparent glass substrate 92 and a 0.25 millimeter thick, transparent, resilient, deformable epoxy layer 94. The readily deformable epoxy layer 94, deforms in response to the pressure of finge ridges $F_r$. The result is to provide a back surface for the platen 84 which provides a high degree of light scattering of whatever light is reflected under the ridge zones and a minimal amount of light scattering of whatever light is reflected under the valley zones $F_v$. As schematically shown in FIGS. 5 and 5A, when the collimated light beam 61 impinges on the relatively flat surface under the valley zone $F_v$, the interface between the epoxy layer 94 and the air under the valleys $F_v$ causes a small portion of the incident light 61 to be reflected, as part of the light beam 63, because of the difference in the index of refraction of the epoxy material 94 and air. Although only about 5% of the incident light is reflected under the valley zones $F_v$, this is sufficient to provide the valley images downstream at the photodiode array 12. Under the finger ridges $F_r$, the highly deformed areas in the highly compliant epoxy material 94 cause a much greater degree of light scatter in the reflected light. The reflected light scatters at angles substantially outside of the angular pass band of the simple imaging lens 65. As a consequence, at the image plane, the valley zones are recreated while the ridge zones are essentially dark.

The result is a clear-cut pattern, received at the array 12 as a slit having alternating light and dark spots. The spots corresponding to the finger valleys are relatively light while the spots corresponding to the ridges are essentially entirely dark.

The scattering depicted by the arrows in FIGS. 5, 5A and 6 is highly schematic. The arrows are not intended to suggest actual angles of scatter but only that the reflected light is scattered.

It is believed that there is some scattering of light under the valley zones $F_v$, but that this scattering is well within the angular pass band of the imaging lens 65 so that substantially all of the reflected light at the valley zone is reflected as collimated light and can be detected by the array 12 at the image plane and at positions displaced from the image plane.

In addition, because of the fact that most fingers carry substantial amounts of finger oil which has an index of refraction very similar to that of the epoxy material 94, there will be substantial absorption of the incident light 61 at the ridge zones $F_r$. Thus, in the FIG. 5 platen, the absorption of light due to index of refraction match will complement the effect of the scattering of light under the ridge zones. However, one advantage of the FIG. 5 platen is that even with a very dry finger, in which there is little or no light absorption at the ridge zones, the substantial scattering of light results in an image downstream that has sufficient differential intensity between the ridge zones and valley zones to provide a usable input for the detecting array 12.

In order for the FIG. 5 platen to operate effectively, it is important that the index of refraction of the epoxy layer 94, or other readily deformable resilient material, be as close as possible to that of the glass 92 or other transparent substrate material that may be used. Matching the index of refraction of the layers 92 and 94 will minimize the amount of light lost by reflection from the interface between the layers 92 and 94. In one embodiment, a transparent optical epoxy is used which is manufactured by Epoxy Technology Inc., 65 Grove Street, Watertown, Mass. 02172 and is designated by the Model No. EPO-TEK No. 305. The index of refraction of this epoxy is 1.511. The epoxy used should be specified as one which when cured will readily deform when pressure in the range of 5 kilograms per square centimeter (about 2 p.s.i.) is applied.

It is also important that the epoxy material 94 be resilient as well as readily deformable so that essentially no latent image will remain in the epoxy once the finger F has been removed.

Furthermore, because the FIG. 5 platen 84 generates finger information by a different physical effect than by optical matching or mis-matching by finger oil causing different reflectivity, the problem of finger oil deposition is of little concern. This eliminates the need to continuously clean the working surface of the platen 84. Accordingly, the cost of the platen 84 as compared with platens previously used is minimal and the cost of operating with the platen 84 is also minimized.

The array 12 is preferably at the image plane. But if it is displaced from the image plane by a small amount it will receive an image. Light spots representing the valleys will appear with an intensity that is a function of a scale factor due to light beam divergence or convergence and that may be affected by a small degree of light scatter that occurs at the valley zones.

THE FIG. 6 PLATEN

The platen of FIG. 6 has four layers. One of the four layers is the five mm. thick transparent glass substrate 92 shown in FIG. 5. The other layers are the 0.25 mm. thick transparent, resilient, compressible epoxy layer 94, a three thousand Angstrom (3,000 A) thick reflective silver layer 96 and a 0.025 mm. thick protective lacquer layer 99. The lacquer layer 99 is the surface layer against which the subject's finger F is pressed. The lacquer layer 99 is quite compliant and the pressure of the finger ridges $F_r$ is transmitted through to the silver layer 96 and epoxy layer 94. From the point of view of the reflected light, it is the reflective silver layer 96 which can be considered as the back surface of the platen. The readily deformable epoxy layer 94 deforms in response to the pressure of the finger ridges $F_r$. The combined operation of the deformable layer 94 and the reflective layer 96 is to provide enhanced contrast between the ridges $F_r$ and the valley $F_v$ of the image of the finger that is reflected downstream from the finger F.

As schematically shown in FIG. 6, when the interrogating light beam 61 impinges on the flat surface of the silver reflective layer 96, it bounces off with an angle of reflection that is equal to the angle of incidence. Thus the light beam portions 63 reflected from the flat surface portions of the silver surface 96 will remain collimated. However, these flat portions of the silver surface 96 are only the portions under the valleys $F_v$ of the applied finger F. As also schematically shown in FIG. 6, under the ridges $F_r$ of the applied finger F, the silver surface 96 is deformed in response to deformation of the deformable, resilient epoxy 94. The rounded reflective surface under these ridges $F_r$ will cause the incident light beam 61 to scatter.

Thus the operation of the FIG. 6 embodiment is similar to that of the FIG. 5 embodiment. One major difference is that in the FIG. 6 platen, the reflective layer 96 assures that the level of light intensity downstream will be very much greater than that provided by the FIG. 5 platen. In particular, the pattern received at the array 12 will have a light intensity determined by the fact that 100% of the incident light is reflected from the FIG. 6 platen as contrasted with the approximately 5% of light reflected in the FIG. 5 platen. A second difference is that because of the moderating effect of the lacquer layer 99, the amount of deformation due to the ridges $F_r$ at the reflective layer 96 is somewhat less than the amount of deformation in the FIG. 5 platen. Accordingly, in the FIG. 6 embodiment, the degree of scatter under the ridges is not quite as great as the degree of scatter under the ridges of the FIG. 5 embodiment. This may be one of the reasons why, in the FIG. 6 embodiment, the array 12 cannot, as a practical matter, be placed at the image plane of the lens 65. The image at the image plane is a fairly uniform bright plane in which whatever distinction there may be between the valleys and ridges cannot be particularly noticed or detected by the array 12. In large part, this is because much of the light scatter under the ridges in the FIG. 6 platen is sufficiently within the angular pass band of the lens 65 so that the reflected light is essentially imaged at the image plane. However, one or two millimeters from the image plane, the scattered light from the rounded areas under the ridges is not properly focused thereby providing a contrast between ridge and valley zones.

What happens is actually not entirely understood by applicant at present. Downstream from the image plane, the defocused ridges appear dark while the substantially collimated light from the valley zones remains quite bright. The contrast between the dark spots and the light spots representing ridges and valleys respectively is a substantial contrast and certainly very much greater than the magnitude of any contrast available from the FIG. 5 platen. Upstream a millimeter or two from the image plane, the valleys, as expected, remain substantially as bright as at the image plane, However, somewhat surprisingly, the ridges achieve a light intensity substantially brighter than that of the valleys.

A flat reflective layer 96 can be achieved when applying and bonding the epoxy layer 94 to the glass substrate 92. When so applying the epoxy, a highly precise, highly flat master can be employed as the means for determining the epoxy surface. In practive, silver is vacuum deposited on a highly flat master glass element. The epoxy (10 to 15 mg.) in liquid form is placed on top of the silver and then the glass substrate 92 is placed on top of the epoxy and held in position 0.23 to 0.25 mm. spaced from the master. When the epoxy is cured, the silver layer 96 lifts off the master glass together with the epoxy layer 94 and glass substrate 92. Lacquer is then sprayed on the silver to provide the layer 99.

The reflective surface 96 of the FIG. 6 platen is held to a high degree of flatness in order to minimize interfering background noice.

Because the reflective layer blocks light from behind it, finger oil has no effect on the operation of the platen and thus noise due to a latent image or other interference is eliminated.

THE FIG. 7 PLATEN.

The FIG. 7 platen is the presently preferred platen. It incorporates two layers in addition to those described in connection with the FIG. 6 platen. These two layers are a second deformable resilient epoxy layer 97 and a second silver layer 98. The silver layer 96 is still the optically active reflective surface.

The layers 94, 96, 97 and 98 in combination form a sandwich which isolates the optically active surface at the layer 96 from the touching surface at the layer 99. This shields the optically active surface, specifically the silver layer 96, from the effects of minute shrinking or expansion caused by temperature changes. Especially, because the optically active reflective layer 96 is in suspension between two of the same materials, the epoxy of layers 94 and 97, it exhibits no external surface effects.

The lacquer layer 99 conforms very readily to the incident finger and provides the durability required to protect the layers beneath it.

A very important factor is that the layers 97, 98 and 99 together perform an important function of smoothing or filtering ridge breaks in the input finger. Thus the topographic map formed on the optically active surface of the layer 96 will be a mechanically filtered, and thus a somewhat idealized, version of the actual finger image. This elimination of certain discontinuities provides for a much simpler signal processing, feature extraction and matching in the downstream electronics.

Fabrication of the FIG. 7 platen is preferably one in which the epoxy layer 94 and the silver layer 96 are initially fabricated against an ultra precise flat master. The silver layer 96 is the release agent for the epoxy layer 94. The silver is initially deposited on this master and is removed with the epoxy layer 94 when the epoxy layer 94 is molded against the master. After the layers 94 and 96 are cured, the layers 97 and 98 are molded again against a precise master with the silver layer 98 acting as a release agent. This second silver layer 98 would not be required except for its function as a release agent in the molding of the second epoxy layer 97. The lacquer layer 99, being very compliant, does not require being placed on with extreme flatness. The epoxy layer is useful not only for its durability in protecting the other layers but also because it operates as part of the mechanical filtering function mentioned above.

In one embodiment, the thickness dimensions of the layers in the FIG. 7 platen are a glass substrate 92 that is nominally 6 mm. thick, a first epoxy layer 94 which is 0.25 mm. thick, a second epoxy layer 97 which is 0.050 mm. thick and a lacquer layer 99 which is 0.025 mm. thick. The two silver layers 96 and 98 are approximately 3,000 Angstroms thick.

The FIG. 7 platen operates very much as does the FIG. 6 platen and the discussion of the FIG. 6 platen applies to the FIG. 7 platen. The FIG. 7 platen is preferred over the FIG. 6 platen primarily because of the improved filtering and better shielding of the reflective layer 96.

The displacement of the array 12 from the image plane is only a relatively slight displacement. In one embodiment employing the FIG. 7 platen, the array 12 has an optimum and preferred position upstream from the image plane. The array 12 position is a function of the quality of the finger image or fingerprint being interrogated. In that embodiment, where a good fingerprint is provided in which the distinctions between the ridges and valleys are quite clear cut, the optimum position of the array 24 is between 0.5 mm. and 0.7 mm. upstream from the image plane where the imaging lens 65 has a 20 mm. focal length. For degraded fingerprints, the optimum position of the array 12 is 2.5 mm. upstream from the image plane. A preferred embodiment of the invention incorporates a mechanism for permitting operator selection of the lesser or greater distance from the image plane by providing two different lenses 65 having slightly different focal lengths. The two lenses 65 are mounted on a movable mount that permits the operator to selectively position one or the other of the two lenses 65 in the path of the modulated reflected light beam 63.

The light intensity at the array 12 upstream from the image plane is three to five times greater at the ridge zones than at the valley zones. It is believed that this observed brilliant intensification which occurs slightly upstream from the image plane comes about because of the combined effects of the non-planarity of the object being imaged and the smooth continuous ridge contours provided by the mechanical filtering due to the layers above the reflective layer 96.

It is presently preferred to deploy the array 12 slightly upstream from the image plane rather than slightly downstream from the image plane because of the noise problem in the relatively dark areas representing the ridge zones downstream. The relatively constant valley zone illumination due to the essentially collimated light provides a minimum noise problem in the valley zones either upstream or downstream from the image plane. However, the distinctive intensification of intensity representing ridge zones upstream of the image plane contrasts with the somewhat noisy relatively dark zones representing the ridges downstream.

It has been observed that the substantial light intensification representing the ridge zones upstream is coupled with a decrease in the width of the ridge zones image. Thus what is observed is a sharp bright line representing the ridge zones at the array 12. The electric field reinforcement which provides this substantially greater intensity at the ridge zones occurs where the collimated light is also coherent. However, where incoherent collimated light is employed as the interrogating light beam 61, the light intensification is also observed. However the extent of the intensification is somewhat less than when coherent light is employed and the significantly distinctive narrowing of the ridge image zones does not occur.

Although some mechanical filtering does occur in connection with the FIG. 6 design, the significant and dramatic improvement in the providing of a stylized image that can be readily processed in provided by the entire multi-layer arrangement shown in FIG. 7. In particular, the second epoxy layer 97 appears to be the element which is the most significant to provide the improved filtering effect.

In a presently preferred embodiment of this invention, the apparatus involved employs the FIG. 1 system with the FIG. 7 platen, in which the platen is stationery and the interrogating beam moves across the finger. That embodiment incorporates the following dimensional relationships. The approximately 1 mm. laser beam is shaped by the lenses 18 and 20 to form a slit beam that is 15 mm. long at the second cylindrical lens 20. The two lenses 18 and 20 are positioned so that their focal points are non coincident. The front focal point of the lens 18 and back focal point of the lens 20 are slightly spaced from one another so that the slit beam converges slightly as it travels downstream from the second cylindrical lens 20. This convergence is only a few degrees so that the slit beam 30 at the platen 23 has a length of about 12 mm. The imaging lens 65 has a 20 mm. focal length and is about 110 mm. downstream from the finger object. The converging slit beam is focused at an image plane, which is about 24 mm. downstream from the lens. The photodiode array 12 plane is one millimeter upstream from the image plane and receives the modulated slit light beam having a length of about 2.3 mm. In that embodiment an array of 256 photocells is employed which has a length of about 3.3 millimeters so that not all of the cells are employed. For degraded fingers, the 20 mm. lens is replaced with one having a 25 mm. focal length. In that case, the distance from the finger object to the lens 65 is about 115 mm., the image plane is 32 mm. from the lens 65 and the array 12 is 4 mm. upstream from the image plane.

THE FIG. 8 PLATEN.

A fourth platen 100 which has been tried with success is illustrated in FIG. 8. In this platen, the glass substrate 92 has, on its back surface, an anti-reflective coating 101. The platen has no other layers. This anti-reflective coating 101 is termed such because it reduces the magnitude of reflection at the interface between air and the back surface of the platen 100. As a consequence, at the interface, all of the incident light, at least ideally, passes through the back surface of the platen and, as shown in FIG. 8, is incident against the valleys for any finger F applied thereon. This coating further calls for the magnitude of reflection at the discontinuity with a further layer of glass (or with a further layer of any substance, such as finger oil, having substantially the index or refraction of glass) to be substantially greater than the magnitude of reflection with the discontinuity of air. The important thing is to have as great a difference between the two magnitudes of reflection as possible, with the reflection at the discontinuity with air being relatively minimal and the reflection at the discontinuity with finger oil being relatively maximal.

With such a platen, it is possible to obtain a usable image at the image plane downstream from the lens 65 regardless of how oily or dry is the finger F. What happens is that if there is appreciable finger oil, then the reflection of the incident light at the ridges is maximum. In one embodiment, about 10% of the incident light is reflected. At the valley zones, essentially no light is reflected from the interface between platen and air. The light reflected from the valleys is so highly scattered that it falls outside of the angular pass band of the lens 65 and thus is not focused.

However, where the finger is extremely dry, there will be a refraction index mismatch under the ridges. But, the ridges themselves reflect the incident light. Because the ridges are pressed against the back surface of the FIG. 8 platen, they are sufficiently flat so that the degree of scatter of the reflected light is within the angular pass band of the lens 65. Thus an image will be formed at the image plane although the brightness of the zones representing the image will be less than when an oily finger is applied to the platen. In this fashion, by use of an anti-reflectant coating 101, the range of fingers which can be processed by the system of this invention is greatly extended because the finger oil is not a prerequisite for the system to interrogate the finger being presented.

Because there is scattering of the reflected light from the ridge zones when a dry finger is applied, there is a great deal of defocusing of the ridge zone light at positions off the image plane. Accordingly, when using a FIG. 8 platen, it is important that the detection array 12 be positioned essentially at the image plane.

FIG. 8 represents a scattering under the ridges although the degree of scatter, like the degree of scatter under the ridges in FIG. 6, is within the angular pass band of the lens 65. By contrast the degree of scatter under the valleys in FIG. 8, like the scatter under the ridges of FIG. 5A, is substantially outside the angular pass band of the lens 65.

One problem with the FIG. 8 type of platen is that the finger oil left by an applied finger can be fixed in place by a charge effect thereby leaving a latent image which will tend to interfere with the next subsequent applied fingerprint. This problem is substantially eliminated by use of an electrically conductive anti-reflective coating 101. Because, the coating 101 is selected to be elecrically conductive, a capacitive charge will not build up across it and thus a latent finger image will not be fixed on the back surface of the platen.

A product designated as No. 7156 from Metavac, Inc. of 44-68 162nd Street, Flushing, New York 11358 is a useful anti-reflectant coating with adequate electrical conductivity. When used as the coating 101, it provides a reflection of substantially under 1% of the incident light at a discontinuity with air; that is, under the valley zones, and a reflection of about 10% at discontinuity with finger oil;; that is, under the ridge zones. With this coating, where a dry finger is applied, the amount of reflected light at the ridges may drop to as little as 5% of the incident interrogating light but that has been found adequate to provide a distinctive image at the image plane.

In general most light sources, whether coherent or incoherent, tend to have a frequency range within which the light is concentrated. The frequency range generally has to be specified as part of the specification for the developemnt of the anti-reflectant coating. The particular Metavac product No. 7156 is employed with a laser having a frequency of 6,328 Angstrom (A).

THE PLATENS COMPARED

An analysis of how the system of this invention operates with the different types of platen arrangements shown requires, in general, consideration of the effects of (a) the extent to which the ridge zones cause scattering of reflected light and (b) the extent to which the finger oil from the ridge zones affects optical matching or mismatching to absorb or reflect indicent light.

Where the reflective layer 96, such as is shown in FIGS. 6 and 7 is employed, the finger oil has no effect. That is one of the advantages of those embodiments.

Other embodiments can be selected so that the scattering cooperates with the oil matching or mismatching effect to provide an enhanced result. Thus in the FIG. 5 embodiment, the optical matching between whatever oil is on the finger and the epoxy layer 94 results in a reduction of reflected light in the ridge zones. Whatever light is reflected is scattered to such a large degree that much of it is outside of the angular pass band of the lens 65 and thus is not reformed at the image plane. Accordingly in the FIG. 5 platen embodiment, light absorption due to the oil and light scattering due to the ridges are reinforcing effects to provide a dark ridge zone at the image plane. Where a very dry finger is involved, so that there is less than the usual amount of absorption due to optical match between oil and epoxy, the high degree of scattering under the ridges tends to assure a usable image in the image plane.

Similarly, in the embodiment shown in FIG. 8, where an oily finger is applied, the anti-reflectant coating 101 causes essentially collimated light reflection under the ridge zones and highly scattered reflection under the valley zones. Where a very dry finger is applied, the light reflected from the relatively flattened ridge zones is refocused to the image plane. Thus whether an oily finger is applied or a very dry finger is applied, there will be a usable and significant ridge zone image at the image plane. In this fashion, light reflection due to the oil and light reflection due to the ridges are reinforcing effects to provide a light ridge zone at the image plane. When contrasting the FIG. 8 platen with the FIG. 5 platen, it must be kept in mind that because of the flattening of the ridge zones the extent of the light scattering from the ridge zones in the FIG. 8 arrangement is substantially less that in the FIG. 5 arrangement so that most of the light scattered from the ridge zones in the FIG. 5 arrangement is outside of the angular pass band of the lens 65 and much of the light reflected from the ridge zones in the FIG. 8 arrangement is within the angular pass band of the lens 65.

What is claimed is:

1. In an optical finger image processing apparatus, the improvement comprising: a platen having a front surface adapted to receive an interrogating light beam and a back surface adapted to receive a finger thereon, said platen having a transparent substrate, a first deformable, resilient transparent layer on the back surface of said substrate, said layer having sufficient thickness and being sufficiently deformable so that forces transmitted by the ridges of a finger pressed against the back surface on said platen will readily cause said layer to deform in the zones directly under the ridges of the applied finger, and a reflective layer on the back surface of said first deformable, resilient layer, said reflective layer being sufficiently thin so that forces transmitted by the ridges of a finger pressed against the back surface of said platen will be readily transmitted to said deformable resilient layer.

2. The improvement of claim 1 wherein said substrate is glass and said first deformable layer is epoxy.

3. The improvement of claim 2 wherein said epoxy layer has a thickness of approximately 0.25 millimeters.

4. The improvement of claims 1, 2 or 3 wherein said reflective layer is a metallic deposit approximately 3,000 Angstroms thick.

5. The improvement of claims 1, 2 or 3 further comprising: a compliant protective layer defining the back surface of said platen.

6. The improvement of claim 4 further comprising: a compliant protective layer defining the back surface of said platen.

7. The improvement of claims 1 or 2 further comprising:
a second deformable, resilient layer on the back surface of said reflective layer to provide a predetermined separation between said reflective layer and the finger receiving surface of said platen.

8. The improvement of claim 7 wherein said second deformable layer has deformation and resilience characteristics comparable to that of said first deformable resilient layer.

9. The improvement of claim 7 further comprising:
a compliant protective layer defining the back surface of said platen.

10. The improvement of claim 8 further comprising:
a compliant protective layer defining the back surface of said platen.

11. In an optical finger image processing apparatus, the improvement comprising: a platen having a front surface adapted to receive an interrogating light beam and a back surface adapted to receive a finger thereon, said platen having a relatively hard transparent substrate, an optically active surface and a touching surface, said optically active surface being effective to reflect substantially all of the incident light received thereon from the interrogating light beam, said platen having a first deformable resilient layer between said substrate and said optically active surface, said first layer being transparent, said platen also having a second deformable resilient layer between said optically active surface and said touching surface, said second layer serving to transmit the three dimensional finger image from said touching surface to said optically active surface, said first layer serving to permit said optically active surface to provide the three dimensional finger image being transmitted.

12. The improvement of claim 11 wherein the deformation and resilience characteristic of said first and second layers are substantially the same.

* * * * *